United States Patent
Kapatoes et al.

(10) Patent No.: US 10,099,067 B2
(45) Date of Patent: Oct. 16, 2018

(54) RADIATION THERAPY DOSE CALCULATION

(71) Applicant: Sun Nuclear Corporation, Melbourne, FL (US)

(72) Inventors: Jeffrey M. Kapatoes, Melbourne, FL (US); Thomas Allen Simon, Rockledge, FL (US); William E. Simon, Melbourne, FL (US)

(73) Assignee: Sun Nuclear Corporation, Melbourne, FL (US)

( * ) Notice: Subject to any disclaimer, the term of this patent is extended or adjusted under 35 U.S.C. 154(b) by 182 days.

(21) Appl. No.: 14/973,570

(22) Filed: Dec. 17, 2015

(65) Prior Publication Data
US 2016/0175613 A1 Jun. 23, 2016

Related U.S. Application Data

(60) Provisional application No. 62/094,513, filed on Dec. 19, 2014.

(51) Int. Cl.
*A61N 5/10* (2006.01)
(52) U.S. Cl.
CPC ......... *A61N 5/1039* (2013.01); *A61N 5/1045* (2013.01); *A61N 5/1071* (2013.01);
(Continued)
(58) Field of Classification Search
CPC ........ A61N 5/1071–5/1075; A61N 2005/1054
See application file for complete search history.

(56) References Cited

U.S. PATENT DOCUMENTS

| 759,608 A | 5/1904 | Harper |
|---|---|---|
| 1,239,145 A | 9/1917 | Wantz |

(Continued)

FOREIGN PATENT DOCUMENTS

| CA | 2718408 | 9/2009 |
|---|---|---|
| DE | 102009039345 A1 | 3/2011 |

(Continued)

OTHER PUBLICATIONS

Brusasco, C, et al. "A Dosimetry System for Fast Measurement of 3D Depth-dose Profiles in Charged-particle Tumor Therapy with Scanning Techniques." *Nuclear Instruments & Methods in Physics Research, Section—B:Beam Interactions With Materials and Atom* 168.4 (2000): 578-92.

(Continued)

*Primary Examiner* — Thaddeus Cox
(74) *Attorney, Agent, or Firm* — Pillsbury Winthrop Shaw Pittman LLP (57) ABSTRACT

Radiation therapy dose calculation methods, systems and computer program products, for use with a treatment delivery device for treating a patient and utilizing a scattered radiation detector in making independent dose calculations. The scattered radiation detector is configured to acquire measurement information during patient treatment, which is used to determine an estimate of the output of the treatment delivery device. Other information is acquired including patient imaging data, gantry angle information and collimator position information utilized during patient treatment. The acquired information is utilized along with the treatment delivery device output estimate to determine dose delivered to the patient.

20 Claims, 2 Drawing Sheets

(52) U.S. Cl.
CPC .... *A61N 5/1075* (2013.01); *A61N 2005/1034* (2013.01); *A61N 2005/1054* (2013.01); *A61N 2005/1055* (2013.01); *A61N 2005/1061* (2013.01)

(56) References Cited

U.S. PATENT DOCUMENTS

| | | |
|---|---|---|
| 2,818,510 A | 12/1957 | Verse |
| 3,033,985 A | 5/1962 | Ben |
| 3,394,258 A | 7/1968 | Schleiger |
| 3,433,953 A | 3/1969 | Sweet |
| 3,665,762 A | 5/1972 | Domen |
| 3,783,251 A | 1/1974 | Pavkovich |
| 3,790,794 A | 2/1974 | Murray |
| 3,980,885 A | 9/1976 | Steward et al. |
| 4,058,832 A | 11/1977 | Vagi |
| 4,063,097 A | 12/1977 | Barrett |
| 4,107,531 A | 8/1978 | Garratt |
| 4,157,472 A | 6/1979 | Barrett |
| 4,312,224 A | 1/1982 | Domen |
| 4,450,440 A | 5/1984 | White |
| 4,455,609 A | 6/1984 | Inamura et al. |
| 4,613,754 A | 9/1986 | Vinegar |
| 4,729,099 A | 3/1988 | Iverson |
| 4,765,749 A | 8/1988 | Bourgade |
| 4,777,442 A | 10/1988 | Rosenthal |
| 4,887,287 A | 12/1989 | Cobben |
| 5,099,505 A | 3/1992 | Seppi et al. |
| 5,160,337 A | 11/1992 | Cosman |
| 5,262,649 A | 11/1993 | Antonuk |
| 5,388,142 A | 2/1995 | Morris |
| 5,394,452 A | 2/1995 | Swerdloff |
| 5,596,653 A | 1/1997 | Kurokawa |
| 5,602,892 A | 2/1997 | Llacer |
| 5,621,214 A | 4/1997 | Sofield |
| 5,627,367 A | 5/1997 | Sofield |
| 5,635,709 A | 6/1997 | Sliski |
| 5,640,436 A | 6/1997 | Kawai |
| 5,661,310 A | 8/1997 | Jones |
| 5,704,890 A | 1/1998 | Bliss et al. |
| 5,712,482 A | 1/1998 | Gaiser et al. |
| 5,873,826 A | 2/1999 | Gono |
| 6,038,283 A | 3/2000 | Carol |
| 6,125,335 A | 9/2000 | Simon |
| 6,131,690 A | 10/2000 | Galando et al. |
| 6,148,272 A | 11/2000 | Bergstrom |
| 6,175,761 B1 | 1/2001 | Frandsen |
| 6,257,552 B1 | 7/2001 | Crow et al. |
| 6,261,219 B1 | 7/2001 | Meloul et al. |
| 6,301,329 B1 | 10/2001 | Surridge |
| 6,345,114 B1 | 2/2002 | Mackie |
| 6,364,529 B1 | 4/2002 | Dawson |
| 6,398,710 B1 | 6/2002 | Ishikawa |
| 6,516,046 B1 | 2/2003 | Froehlich |
| 6,535,756 B1 | 3/2003 | Simon et al. |
| 6,552,347 B1 | 4/2003 | Dimcovski |
| 6,560,311 B1 | 5/2003 | Shepard |
| 6,594,336 B2 | 7/2003 | Nishizawa |
| 6,609,626 B2 | 8/2003 | Young |
| 6,609,826 B1 | 8/2003 | Fujii et al. |
| 6,626,569 B2 | 9/2003 | Reinstein |
| 6,636,622 B2 | 10/2003 | Mackie |
| 6,648,503 B2 | 11/2003 | Tanaka |
| 6,712,508 B2 | 3/2004 | Nilsson |
| 6,788,759 B2 | 9/2004 | Op De Beek |
| 6,799,068 B1 | 9/2004 | Hartmann et al. |
| 6,810,107 B2 | 10/2004 | Steinberg |
| 6,810,108 B2 | 10/2004 | Clark |
| 6,839,404 B2 | 1/2005 | Clark |
| 6,853,702 B2 | 2/2005 | Renner |
| 6,888,919 B2 | 5/2005 | Graf |
| 6,904,119 B2 | 6/2005 | Oikawa |
| 6,904,125 B2 | 6/2005 | Van Dyk |
| 6,904,162 B2 | 6/2005 | Robar |
| 6,974,254 B2 | 12/2005 | Paliwal |
| 6,990,368 B2 | 1/2006 | Simon et al. |
| 6,992,309 B1 | 1/2006 | Petry |
| 7,016,454 B2 | 3/2006 | Warnberg |
| 7,065,812 B2 | 6/2006 | Newkirk et al. |
| 7,076,023 B2 | 7/2006 | Ghelmansarai |
| 7,098,463 B2 | 8/2006 | Adamovics |
| 7,116,749 B2 | 10/2006 | Besson |
| 7,127,028 B2 | 10/2006 | Sendai |
| 7,127,030 B2 | 10/2006 | Tamegai |
| 7,142,634 B2 | 11/2006 | Engler |
| 7,193,220 B1 | 3/2007 | Navarro |
| 7,221,733 B1 | 5/2007 | Takai |
| 7,233,688 B2 | 6/2007 | Ritt |
| 7,234,355 B2 | 6/2007 | Dewangan |
| 7,298,820 B2 | 11/2007 | Nelson |
| 7,339,159 B2 | 3/2008 | Juh |
| 7,349,523 B2 | 3/2008 | Jenkins |
| 7,352,840 B1 | 4/2008 | Nagarkar |
| 7,371,007 B2 | 5/2008 | Nilsson |
| 7,386,089 B2 | 6/2008 | Endo |
| 7,420,160 B2 | 9/2008 | Delaperriere |
| 7,453,976 B1 | 11/2008 | Yin |
| 7,471,765 B2 | 12/2008 | Jaffray |
| 7,515,681 B2 | 4/2009 | Ebstein |
| 7,579,608 B2 | 8/2009 | Takahashi et al. |
| 7,605,365 B2 | 10/2009 | Chen |
| 7,668,292 B1 | 2/2010 | Bose |
| 7,734,010 B2 | 6/2010 | Otto |
| 7,750,311 B2 | 7/2010 | Daghighian |
| 7,766,903 B2 | 8/2010 | Blumenkranz |
| 7,773,723 B2 | 8/2010 | Nord |
| 7,778,383 B2 | 8/2010 | Koehler |
| 7,778,392 B1 | 8/2010 | Berman |
| 7,778,680 B2 | 8/2010 | Goode, Jr. |
| 7,782,998 B2 | 8/2010 | Langan |
| 7,945,022 B2 | 5/2011 | Nelms et al. |
| 8,044,359 B2 | 10/2011 | Simon |
| 8,093,549 B2 | 1/2012 | Navarro |
| 8,130,905 B1 | 3/2012 | Nelms |
| 8,136,773 B2 | 3/2012 | Schmutzer et al. |
| 8,147,139 B2 | 4/2012 | Papaioannou |
| 8,218,718 B1 | 7/2012 | Van Herk et al. |
| 8,235,530 B2 | 8/2012 | Maad |
| 8,242,458 B2 | 8/2012 | Rinecker et al. |
| 8,321,179 B2 | 11/2012 | Simon et al. |
| 8,325,878 B2 | 12/2012 | McNutt |
| 8,430,564 B2 | 4/2013 | Simmons et al. |
| 8,457,713 B2 | 6/2013 | Kagermeier |
| 8,474,794 B2 | 7/2013 | Liljedahl |
| 8,536,547 B2 | 9/2013 | Maurer, Jr. et al. |
| 8,541,756 B1 | 9/2013 | Treas |
| 8,605,857 B1 | 12/2013 | Renner |
| 8,632,448 B1 | 1/2014 | Schulte |
| 8,726,814 B1 | 5/2014 | Matteo |
| 8,794,899 B2 | 8/2014 | Cozza et al. |
| 8,833,709 B2 | 9/2014 | Weng |
| 8,840,304 B2 | 9/2014 | Perez Zarate et al. |
| 8,840,340 B2 | 9/2014 | Eisenhower |
| 8,874,385 B2 | 10/2014 | Takayanagi et al. |
| 8,927,921 B1 | 1/2015 | Nelms et al. |
| 9,050,460 B2 | 6/2015 | Hildreth et al. |
| 9,097,384 B2 | 8/2015 | Simon et al. |
| 9,463,336 B2 | 10/2016 | Nelms |
| 9,480,861 B2 | 11/2016 | Kapatoes |
| 9,561,388 B2 | 2/2017 | Hildreth |
| 9,586,060 B2 | 3/2017 | Seuntjens |
| 9,750,955 B2 | 9/2017 | McNutt |
| 2001/0042841 A1 | 11/2001 | Lyons |
| 2002/0077545 A1 | 6/2002 | Takahashi |
| 2002/0080912 A1 | 6/2002 | Mackie |
| 2003/0043879 A1 | 3/2003 | Tanaka |
| 2003/0043960 A1 | 3/2003 | Op De Beek |
| 2003/0138077 A1 | 7/2003 | Lee |
| 2003/0231740 A1 | 12/2003 | Paliwal |
| 2004/0066880 A1 | 4/2004 | Oikawa |
| 2004/0068182 A1 | 4/2004 | Misra |
| 2004/0096033 A1 | 5/2004 | Seppi |
| 2004/0113094 A1 | 6/2004 | Lyons |
| 2004/0120560 A1 | 6/2004 | Robar |

(56) References Cited

U.S. PATENT DOCUMENTS

| | | |
|---|---|---|
| 2004/0211917 A1 | 10/2004 | Adamovics |
| 2004/0228435 A1 | 11/2004 | Russell |
| 2004/0251419 A1 | 12/2004 | Nelson |
| 2005/0013406 A1 | 1/2005 | Dyk |
| 2005/0077459 A1 | 4/2005 | Engler |
| 2005/0111621 A1 | 5/2005 | Riker et al. |
| 2006/0002519 A1 | 1/2006 | Jenkins |
| 2006/0033044 A1 | 2/2006 | Gentry |
| 2006/0184124 A1 | 8/2006 | Cowan |
| 2006/0203964 A1 | 9/2006 | Nyholm |
| 2006/0203967 A1 | 9/2006 | Nilsson |
| 2006/0266951 A1 | 11/2006 | Fritsch |
| 2007/0041497 A1 | 2/2007 | Schnarr |
| 2007/0041499 A1 | 2/2007 | Lu et al. |
| 2007/0071169 A1 | 3/2007 | Yeo |
| 2007/0081629 A1 | 4/2007 | Yin |
| 2007/0086577 A1 | 4/2007 | Kobayashi |
| 2007/0195930 A1 | 8/2007 | Kapatoes |
| 2008/0031406 A1 | 2/2008 | Yan et al. |
| 2008/0049896 A1 | 2/2008 | Kuduvalli |
| 2008/0049898 A1 | 2/2008 | Romesberg, III |
| 2008/0091388 A1 | 4/2008 | Failla |
| 2008/0103834 A1 | 5/2008 | Reiner |
| 2008/0118137 A1 | 5/2008 | Chen et al. |
| 2008/0260368 A1 | 10/2008 | Chang |
| 2008/0292055 A1 | 11/2008 | Boone |
| 2009/0003512 A1 | 1/2009 | Pouliot |
| 2009/0067576 A1* | 3/2009 | Maltz .............. A61N 5/1048 378/65 |
| 2009/0090870 A1 | 4/2009 | Ahnesjo |
| 2009/0175418 A1* | 7/2009 | Sakurai ............ A61N 5/1048 378/98.5 |
| 2009/0217999 A1 | 9/2009 | Becker |
| 2009/0227841 A1 | 9/2009 | Miyako |
| 2009/0250618 A1 | 10/2009 | Simon |
| 2009/0252292 A1 | 10/2009 | Simon |
| 2011/0022360 A1 | 1/2011 | Simon |
| 2011/0051893 A1 | 3/2011 | McNutt |
| 2011/0096906 A1 | 4/2011 | Langeveld |
| 2011/0158386 A1 | 6/2011 | Payne |
| 2011/0210258 A1 | 9/2011 | Black |
| 2011/0248188 A1 | 10/2011 | Brusasco et al. |
| 2011/0278444 A1* | 11/2011 | Navarro ................ G01T 1/02 250/252.1 |
| 2011/0306864 A1 | 12/2011 | Zarate et al. |
| 2012/0014618 A1 | 1/2012 | Sun et al. |
| 2012/0025105 A1 | 2/2012 | Brown et al. |
| 2012/0292517 A1 | 11/2012 | Izaguirre |
| 2012/0305793 A1* | 12/2012 | Schiefer .......... A61N 5/1048 250/394 |
| 2012/0326057 A1 | 12/2012 | Remeijer et al. |
| 2013/0048883 A1 | 2/2013 | Simon et al. |
| 2013/0303902 A1 | 11/2013 | Smith |
| 2014/0073834 A1 | 3/2014 | Hildreth et al. |
| 2014/0094642 A1 | 4/2014 | Fuji |
| 2014/0105355 A1 | 4/2014 | Toimela |
| 2014/0263990 A1 | 9/2014 | Kawrykow et al. |
| 2015/0080634 A1* | 3/2015 | Huber .............. A61N 5/1075 600/1 |
| 2015/0087879 A1 | 3/2015 | Nelms |
| 2015/0238778 A1 | 8/2015 | Hildreth et al. |
| 2015/0283403 A1 | 10/2015 | Kapatoes et al. |
| 2015/0309193 A1 | 10/2015 | Kozelka et al. |
| 2016/0067479 A1 | 3/2016 | Marcovecchio |
| 2016/0166857 A1 | 6/2016 | Nelms |
| 2017/0021194 A1 | 1/2017 | Nelms |

FOREIGN PATENT DOCUMENTS

| | | |
|---|---|---|
| EP | 1060726 | 12/2000 |
| EP | 1060726 B1 | 6/2004 |
| EP | 2016445 | 1/2009 |
| EP | 2078537 A1 | 7/2009 |
| EP | 2117649 A2 | 11/2009 |
| EP | 2186542 | 5/2010 |
| EP | 2457237 | 5/2012 |
| EP | 2708919 A2 | 3/2014 |
| EP | 2865417 | 4/2015 |
| EP | 3074088 | 10/2016 |
| JP | 05-154209 | 6/1993 |
| JP | 2003310590 A | 11/2003 |
| JP | 2008105882 | 5/2008 |
| JP | 2010215428 | 9/2010 |
| JP | 2010234521 | 10/2010 |
| WO | 2006138513 | 12/2006 |
| WO | 2008013956 | 1/2008 |
| WO | 2009114669 | 9/2009 |
| WO | 2009120494 | 10/2009 |
| WO | 2009137794 | 11/2009 |
| WO | 2011011471 | 1/2011 |
| WO | 2012053440 | 4/2012 |
| WO | 2013049839 | 4/2013 |
| WO | 2013177677 | 12/2013 |
| WO | 2015024360 | 2/2015 |
| WO | 2015073899 | 5/2015 |
| WO | 2016172352 | 10/2016 |

OTHER PUBLICATIONS

Nelms, Benjamin. "Variation in External Beam Treatment, Plan Quality: An Inter-institutional Study of Planners and Planning Systems." Practical Radiation Oncology 2.4 (2012): 296-305.

"Hi-Art,"; www.tomotherapy.com; TomoTherapy, Madison, WI; 2007; pp. 1-8.

"Rapid Arc"; Varian Medical Systems, Inc., Palo Alto, CA; www.varian.com; 2007; pp. 1-8.

"VMAT"; Elekta,Ltd., Crawley UK; Document No. 4513 3710770; Oct. 8, 2008.

"Waterphantom Dosimetry"; Medical Physics, vol. 3, May/Jun. 1976; pp. 189.

Ahnesjo et al. Phys. Med. Biol. 44, R99-R155 1999.

Ahnesjo et al., Acta. Oncol., 26, 49-56, 1987.

Ahnesjo, Med. Phys. 16, 577-92, 1989.

Albers et al., CRC HAndbook of Chemistry and Physics, 87th Ed., Edited by R.C. Weast (CRC, Cleveland, 1976. pp. F-11, D-171, E-6.

Almond et al. In "AAPM TG-51 Protocol for Clinical Reference Dosimetry of Hign Energy Photon and Electron Beams" (Med. Phys. VI, 26, pp. 1847-1870, 1999.

Amanatides et al., Eurographics '87, Conference Proceedings, 1987.

Aspen Aerogels, Pyrogel.RTM. 2250 Datasheet (Aspen Aerogels, Inc., Northborough, 2010).

Benedick Fraass; "Quality Assurance for Clinical Radiotherapy Treatment Planning," Med Phys., 25(10), Oct. 1998; pp. 1773-1829.

Berlyand et al., "Portable Calorimeter for Measuring Absorbed Doses of X-Rays and Electrons from Accelerators", translated from Izeritel'naya Teknika, No. 11, Nov. 1991, pp. 56-58.

Boutillon in "Gap Correction for the Calorimetric Measurement of Absorbed Dose in Graphite with a 60Co Beam" (Phys. Med. Biol., vol. 34, pp. 1809-1821, 1989.

Cyberknife; Cyberknife Systems; "The Standard of Radiosurgery" by Accuracy, Sunnyvale, CA; 2009; pp. 1-6.

D.W.O. Rogers; "Montey Carlo Techniques in Radiotherapy,"; Physics in Canada, Medical Physics Special Issue, v. 58 #2; 2002; pp. 63-70.

Daures et al., "New Constant-Temperature Operating Mode for Graphite Calorimeter at LNE-LNHB", Physics in Medicine and Biology, vol. 50, 2005, No. pp. 4035-4052.

Daures et al., "Small section graphite calorimeter (CR10) at LNE-LNHB for measurement in small beams for IMRT", Metrologica, (Dec. 1, 2011), XP020229547.

Daures et al., "Small Section Graphite Calorimeter (GR-10) at LNE-LNHB for Measurements in Small Beams for IMRT Metrologia", vol. 49, No. 5, 2012, pp. S174-S178.

Domen et al., "A Heat-loss-Compensated Calori meter: Theory, Design, and Performance", Journal of Research of the National Bureau of Standards—A. Physics and Chemistry, vol. 78A, No. 5, Sep.-Oct. 1974, pp. 595-610.

(56) References Cited

OTHER PUBLICATIONS

Domen, "Absorbed Dose Water Calorimeter" (Med. Phys., vol. 7, pp. 157-159).
Duane et al., "An Absorbed Dose Calorimeter for IMRT Dosimetry", Metrologia, vol. 49, No. 5, 2012, pp. S168-S173.
EP2277353 Search Report dated Jul. 21, 2017.
EP2457237 Supplemental European Search Report and Written Opinion dated Mar. 8, 2017.
G.J. Kutcher; "Comprehensive AQ for Radiation Oncology Report;" AAPM Radiation Therapy Committee Task Group 40; Med. Phys., 21; Apr. 1994; pp. 581-618.
IAEA, TRS., "398. Absorbed Dose Determination in External Beam Radiotherapy: An International Code of Practice for Dosimetry based on Standards of Absorbed Dose to Water," Vienna International Atomic Energy Agency (2000).
Indra J. Das, Chee-Wai Cheng, Ronald J. Watt, Anders Ahnesjo, John Gibbons, X. Allen Li, Jessica Lowenstien, Raj K. Mitra, William E. Simon, Timothy C. Zhu; Accelerator Beam Data Commissioning Equiptment and Procedures; Report of the TG-106 of the Therapy Physics Committee of the AAPM; Med. Phys. 35(9), Sep. 2008; pp. 4186-4215.
J. Seuntjens and S. Duane, "Photon absorbed dose standards," Metrologia 46, S39-S58 (2009).
Joseph O. Deasy; "A Computational Environment for Radiotherapy Research," Med. Phys. 30, (5), May 2003; pp. 979-985.
Kawrakow et al. In "The EGSnrc Code System: Monte-Carlo Simulation of Electron and Photon Transport" (Canadian National Research Center, NRC Report PIRS-701, 2006.
Liu et al., Med. Phys. 24, 1729-1741, 1997.
Lu et al., Phys. Med. Biol. 50, 655-680, 2005.
Mackie et al., Med. Phys. 12, 188-196, 1985.
Mackie et al., Phys. Med. Biol. 33, 1-20, 1988.
Mackie et al., Use of Comp. In Rad. Ther., 107-110 1987.
MapCALC; www.sunnuclear.com; manufactured by Sun Nuclear Corp.; Melbourne, FL; 2009.
MapCheck and EPIDose; www.sunnuclear.com; manufactured by Sun Nuclear Corp.; Melbourne,FL; 2010.
Mathilda Van Zijtveld, Maaretn L.P. Dirkxa, Hans C.J. De Boera, and Ben J.M. Heijmen; "3D Dose Reconstruction for Clinical Evaluation of IMRT Pretreatment Verification with an EPID." Radiotherapy and Oncology, 82(2); Feb. 2007; pp. 201-201.
Mc Ewen at al., 'A Portable Calorimeter for Measuring Absorbed Dose in the Radiotherapy Clinic', Physics in Medicine and Biology, vol. 45, No. 12, Dec. 2000, pp. 3675-3691.
McDonald et al., "Portable Tissue Equivalent Calorimeter", Medical Physics, vol. 3, 2, Mar.-Apr. 1976, pp. 80-86.
McEwen et al., Portable Graphite Calorimeter for Measuring Absorbed Dose in the Radiotherapy Clinic.Standards and Codes of Practice in Medical Radiation Dosimetry,IAEA-CN-96-9P,2002, pp. 115-121.
Miller, "Polystyrene Calorimeter for Electron Beam Dose Measurements", Radiation Physics Chemistry vol. 46, No. 4-6, Aug. 1995, pp. 1243-1246.
Mohan et al., Med. Phys. 12, 592-597, 1985.
Myers et al., "Precision Adiabatic Gamma-Ray Calorimeter using Thermistor Thermometry", Review of Scientific Instruments, vol. 32, No. 9, Sep. 1961, pp. 1013-1015.
Nutbrown et. "Evaluation of Factors to Convert Absorbed Dose Calibrations in Graphite to Water for Mega-Voltage Photon Beams" (UK National Pysical Laboratory, NPL Report CIRM 37, 2000.
Ostrowsky et al., "The Construction of the Graphite Calorimeter GR9 at LNE-LNHB (Geometrical and technical considerations)", Report CEA-R-6184, 2008, 52 pages.
Otto, Med. Phys. 35, 310-317, 2008.
Owen et al "Correction for the Effect of the Gaps around the Core of an Absorbed Dose Graphite Calorimeter in High Energy Photon Radiation" (Phys. Med. Biol., vol. 36, pp. 1699-1704, 1991.
Palmans et al., "A Small-Body Portable Graphite Calorimeter for Dosimetry in Low-Energy Clinical Proton Beams", Physics in Medicine and Biology, vol. 49, No. 16, Aug. 2004, pp. 3737-3749.
Papanikolaou et al., Med. Phys. 20, 1327-1336, 1993.
PCT App. No. PCT/US2009/036775; International Preliminary Report on Patentability Chapter II and Written Opinion dated Sep. 12, 2010.
PCT App. No. PCT/US2009/036775; International Search Report dated Nov. 12, 2009.
PCT App. No. PCT/US2009/036917; International Preliminary Report on Chapter II Patentability dated Mar. 15, 2011.
PCT App. No. PCT/US2009/036917; International Search Report dated Sep. 17, 2009.
PCT App. No. PCT/US2009/036917; Written Opinion dated Sep. 12, 2010.
PCT App. No. PCT/US2009/043341; International Preliminary Report on Patentability Chapter I dated Nov. 9, 2010.
PCT App. No. PCT/US2009/043341; International Search Report dated Jan. 5, 2010.
PCT App. No. PCT/US2009/043341; Written Opinion of the International Search Authority dated Nov. 8, 2010.
PCT App. No. PCT/US2010/042680; International Preliminary Report on Patentability Chapter I dated Jan. 24, 2012.
PCT App. No. PCT/US2010/042680; International Search Report dated Jan. 27, 2011.
PCT App. No. PCT/US2010/042680; International Written Opinion dated Jan. 23, 2012.
PCT App. No. PCT/US2012/053440; International Preliminary Report on Patentability Chapter I dated Mar. 3, 2015.
PCT App. No. PCT/US2012/053440; International Search Report and Written Opinion dated Mar. 26, 2014.
PCT App. No. PCT/US2012/058345; International Preliminary Report on Patentability Chapter I dated Apr. 1, 2014.
PCT App. No. PCT/US2012/058345; International Search Report dated Apr. 17, 2013.
PCT App. No. PCT/US2012/058345; International Written Opinion of the International Search Authority dated Mar. 29, 2014.
PCT App. No. PCT/US2014/065808; International Preliminary Report on Patentability Chapter I dated May 17, 2016.
PCT App. No. PCT/US2014/065808; International Search Report and Written Opinion dated May 21, 2015.
PCT App. No. PCT/US2015/024360; International Preliminary Report on Patentability Chapter I dated Oct. 4, 2016.
PCT App. No. PCT/US2015/024360; International Search Report and Written Opinion dated Oct. 8, 2015.
PCT App. No. PCT/US2016/028664; International Preliminary Report on Patentability dated Nov. 2, 2017.
PCT/US2017/044472; International Search Report and Written Opinion of the International Searching Authority, or the Declaration dated Oct. 13, 2017.
Petree et al., "A Comparison of Absorbed Dose Determinations in Graphite by Cavity Ionization Measurements and by Calorimetry", Journal of Research of the National Bureau of Standards—C. Engineering and Instrumentation. vol. 71 C, No. 1, Jan.-Mar. 1967, pp. 19-27.
Picard et al., "Construction of an Absorbed-Dose Graphite Calorimeter", Report BIPM-09/01' May 2009, 12 pages.
R. Alfonso et al., 'A new formalism for reference dosimetry of small and nonstandard fields,' Med. Phys. 35, 5179-5186 (2008).
Renaud et al., "Development of a graphite probe calorimeter for absolute clinical dosimetry", Med. Phvs., (Jan. 9, 2013), vol. 40, No. 2, p. 020701, XP012170941.
Robert M. Eisberg; "Fundamentals of Modern Physics," Chapter 9—Perturbation Theory; John Wiley & Sons; 1967; pp. 268-272.
Rogers, "The physics of AAPM's TG-51 protocol," in Clinical Dosimetry Measurements in Radiotherapy, Medical Physics Monograph No. 34, edited by D. W. O. Rogers and J. E. Cygler (Medical Physics Publishing, Madison, WI, 2009), pp. 239-298.
Ross et al. In "Water Calorimetry for Radiation Dosimetry" (Phys. Med. Biol., vol. 41, pp. 1-29).
S. Picard, D. T. Burns, and P. Roger, "Determination of the specific heat capacity of a graphite sample using absolute and differential methods," Metrologia 44, 294-302 (2007).
Sander et al., "NPL's new absorbed dose standard for the calibration of HDR 192lr brachytherapy sources," Metrologia 49, S184-S188 (2012).

(56) References Cited

OTHER PUBLICATIONS

Seuntjens et al., Review of Calorimeter Based Absorbed Dose to Water Standards, Standards and Codes of Practice in Medical Radiation Dosimetry, IAEA-CN-96-3,2002 p. 37-66.
Stewart in "The Development of New Devices for Accurate Radiation Dose Measurement: A garded Liquid Ionization Chamber and an Electron Sealed Water Calorimeter" (Ph. D. Dissertation McGill University, 2007.
Sundara et al., "Graphite Calorimeter in Water and Calibration of Ionization Chambers in Dose to Water for 60Co Gamma Radiation", Medical Physics, vol. 7, No. 3, May-Jun. 1980, pp. 196-201.
T.R. McNutt, T.R. Mackie, P.J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.
Williams, SIGGRAPH Comput. Graph. 17, 3, 1-11, 1983.
Witzani et al., "A Graphite Absorbed-Dose Calorimeter in the Quasi-Isothermal Mode of Operation", Metrologia, vol. 20, No. 3, 1984, pp. 73-79.
Y. Morishita et al., "A standard for absorbed dose rate to water in a 60Co field using a graphite calorimeter at the national metrology institute of Japan," Radiat. Prot. Dosim. 1-9 (2012) (published E-first Sep. 5, 2012).
Yan et al., Phys. Med. Biol. 42, 123-132, 1997.
Yu, Phys. Med. Biol. 40, 1435-1449, 1995.

\* cited by examiner

RADIATION THERAPY DOSE CALCULATION

CROSS-REFERENCE TO RELATED APPLICATIONS

The current application claims priority to provisional application No. 62/094,513 filed Dec. 19, 2014, which is incorporated by reference in its entirety.

TECHNICAL FIELD

The present disclosure relates to radiation therapy quality assurance.

BACKGROUND

Radiation therapy may be used to treat particular conditions within a patient, for example, to kill malignant cells. Damaging radiation is often delivered by an external beam that can be generated by a linear accelerator (linac). Modern radiation therapy systems are extremely complex and rely on even more complex measurement devices and calculations in order to provide proper dose to the proper location within a patient. Because of these systems' complexity and the importance of ensuring a patient is receiving the prescribed dose, there exists a need for methods and systems for independent measurement and verification of the dose delivered to a patient during radiation therapy.

SUMMARY

In one aspect, a radiation therapy dose calculation system for use with a treatment delivery device for treating a patient includes a scattered radiation detector and an independent dose calculator. The scattered radiation detector is configured to acquire measurement information during patient treatment. The independent dose calculator is configured to acquire measurement information from the scattered radiation detector, determine an estimate of the output of the treatment delivery device from the scattered radiation detector's acquired measurement information, acquire gantry angle and collimator position information utilized during patient treatment, receive patient imaging data, and calculate a delivered dose to the patient utilizing the gantry angle position information, collimator position information, patient imaging data, and the estimate of the output of the treatment delivery device.

In some variations, one or more of the following features can optionally be included in any feasible combination.

The independent dose calculator can be configured to acquire gantry angle and collimator position information from a log file associated with the treatment delivery device. The independent dose calculator can also be configured to acquire collimator position information from an electronic portal imaging device. The independent dose calculator further can be configured to calculate delivered dose to the patient utilizing Monte Carlo or convolution/superposition methods. The imaging data can include CT data or MRI data.

The gantry angle information can be acquired from an inclinometer. The scattered radiation detector can include a radiation sensitive diode and shielding to limit the directions from which radiation is detected.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to, a connection over a network (e.g., the Internet, a wireless wide area network, a local area network, a wide area network, a wired network, or the like), via a direct connection between one or more of the multiple computing systems, etc.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
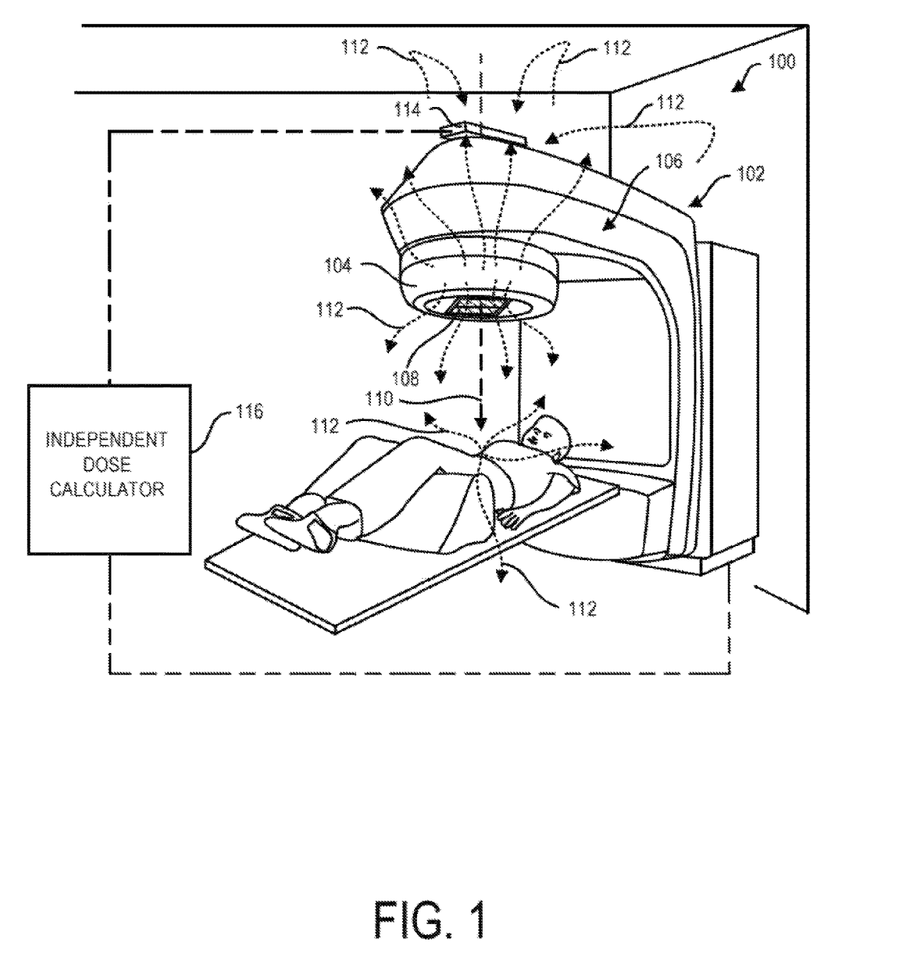
FIG. 1 is a simplified diagram illustrating aspects of a system consistent with implementations of the current subject matter.

Referring to FIG. 1, according to one embodiment of the present disclosure, a radiotherapy system 100 includes a treatment delivery device 102 including a head 104 that can rotate on gantry 106. The treatment delivery device 102 may be any type of radiation therapy device, such as a linear accelerator (linac), proton-generating cyclotron or synchrotron. The treatment delivery device 102 may also include collimators 108 that may be used to shape a treatment beam generally propagating along treatment beam axis 110. There can be additional independent systems included with the treatment delivery device, for example, beam monitors, diagnostic systems, control systems, data acquisition systems, etc. In the typical operation of a treatment delivery device 102, in addition to the radiation propagated by the treatment beam itself, there will exist scattered radiation 112. When the present disclosure refers to "scattered radiation," the term is intended to include radiation other than the treatment beam itself, such as scattered radiation originating from the treatment beam as well as leakage radiation that penetrates through components of the treatment head.

FIG. 1 also includes a scattered radiation detector 114. This detector is designed to measure scattered radiation 112. Scattered radiation detector 114 can be any type of radiation detector, for example, radiation sensitive diodes, ionization chambers, scintillation-based detectors, etc. Scattered radiation detector 114 may include multiple detectors and multiple types of detectors.

In one implementation, shielding may be installed on portions of scattered radiation detector 114 so as to limit the sensing of scattered radiation to that coming from a particular direction or directions.

Scattered radiation detector 114 may include additional components such as an electrometer, a processor, and a communication device. In one embodiment, scattered radiation detector 114 may include a wireless communication device enabling the detector to communicate measurement information to another device.

The scattered radiation detector 114 may be battery operated, for example, if located on head 104, or it may plug into a standard AC outlet if in a location where a cord would not cause interference with treatment delivery device 102.

Because scattered radiation detector 114 is intended to detect scattered radiation 112 and not radiation of the treatment beam itself, it is located outside the path of the treatment beam (i.e., the beam intended to treat the patient). Aside from being outside of the treatment beam, scattered radiation detector 114 can be mounted anywhere proximate the treatment area, on head 104, on any other part of treatment delivery device 102, or completely off of treatment delivery device 102, for example, on a wall of the treatment vault.

When properly calibrated, measurement information from scattered radiation detector 114 can be used to estimate the output of the treatment delivery device (prior to any collimators). The calibration process correlates the output of the treatment delivery device (preferably directly measured without a patient present) with measurement information obtained from scattered radiation detector 114. The relationship between the scattered radiation detector measurement information and the treatment delivery device output will primarily depend upon the actual output of the treatment delivery device and secondarily on other parameters such as treatment field size, amount of scattering material in the beam (e.g., size of the patient), and distance of the scattered radiation detector from the source.

In one preferred implementation, scattered radiation detector 114 can be mounted on head 104, approximately co-linear with the treatment beam axis 110, as shown in FIG. 1.

In another preferred implementation, scattered radiation detector 114 is mounted in any location on treatment delivery device 102 that rotates with the gantry, and that also ensures that the detector is not in the direct path of the treatment beam. Such placement on a rotating portion of the device ensures a constant positioning of the scattered radiation detector 114 with respect to the treatment beam and head 104 during gantry rotation and may help reduce the complexity of the calibration over a placement not on the rotating gantry (by limiting the dependence on secondary parameters (field size, patient size, distance to detector).

An exemplary calibration process may involve mounting and setting up scattered radiation detector 114, including confirming that the bias voltage on the electrometer is in an acceptable range and that the detector is able to transmit its measurement information. Next, an ion chamber or other reference beam measurement device can be placed in the path of the treatment beam. A fixed number of monitor units can be delivered (directed at the reference beam measurement device) while, at the same time, measurement information is gathered from scattered radiation detector 114. A calibration factor can be then calculated based on data from the scattered radiation detector 114 and data from the reference detector placed in the path of the treatment beam.

If scattered radiation detector 114 is mounted in a location off of the rotating portion of the treatment delivery device 102, the calibration process must be completed at a number of different gantry angles to determine how the correlation will vary due to the changing distance between scattered radiation detector 114 and head 104, the different angles of incidence of the scattered radiation, etc. The calibration process may also require knowledge of the scatter detector response with varying field size as well as incorporation of the size of the patient through such means as measurements with varying thicknesses of water, solid water or the like.

FIG. 1 also depicts independent dose calculator 116, which may include a computing device with communication abilities and software that is independent of the treatment delivery device 102 itself.

In one embodiment, the independent dose calculator 116 is capable of receiving measurement information from scattered radiation detector 114 and, using the previously determined calibration information, determine an estimate of the output for treatment delivery device 102. Alternatively, scattered radiation detector 114 may itself include a processor capable of making the estimated output determination.

The independent dose calculator 116 is also capable of acquiring gantry angle information, collimator position information and patient imaging data. Such information may come from the treatment delivery device 102 itself, from other independent systems, or some combination therein. For example, in one embodiment, collimator position information is derived from a time series of images acquired by detectors residing behind the patient and capturing information on the beam that exits the patient. In another embodiment, the collimator position information is taken from treatment delivery device log files. In further embodiments, the patient imaging data used for the dose calculation is acquired by a CT imaging system integrated with the treatment delivery device 102 before, during or after the treatment. In other embodiments, the patient imaging data is acquired by an MRI-system integrated into the treatment delivery device before, during, or after the treatment. In other embodiments, gantry angle information may be obtained from an inclinometer. Such inclinometers may be a device attached to the gantry, a camera-type inclinometer observing gantry motion from a position away from the gantry, or other devices capable of determining gantry angle.

The independent dose calculator 116 may then use time-synchronized gantry angle, collimator position and scattered radiation detector 114 measurement information, along with previously acquired patient image data, to compute the dose delivered to a patient during treatment. Dose calculation may be completed using Monte Carlo, convolution/superposition or other methods.

Figure 2:
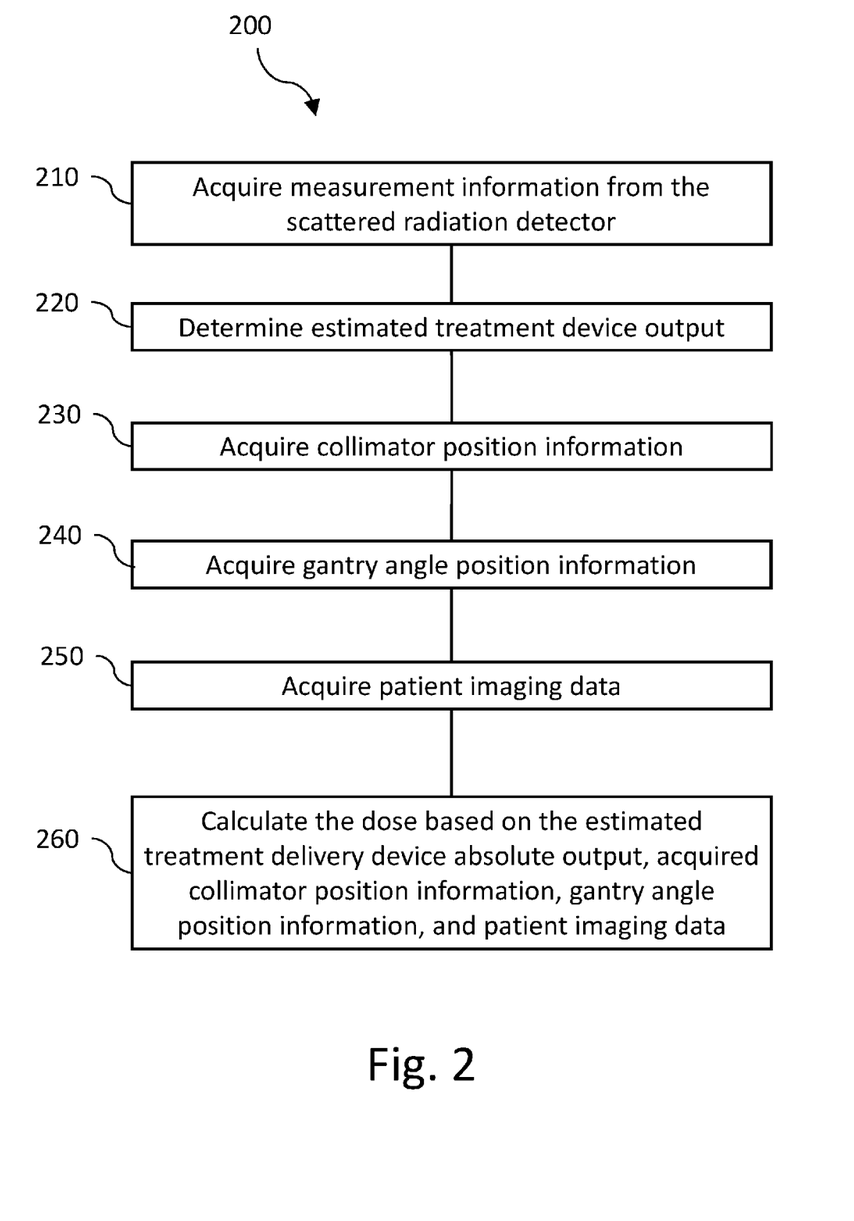
FIG. 2 is a process flow diagram illustrating a method for calculating a dose received by a patient from a treatment delivery device.

FIG. 2 is a process flow diagram 200 illustrating a method for calculating dose received by a patient from a treatment delivery device. The steps described below in 210-260 need not be performed in any particular order or sequence, and should not be construed to be limited to any defined order of execution.

At 210, measurement information can be acquired from scattered radiation detector 114. The measurement information can include, for example, time traces of voltages, currents, or other processed data from scattered radiation detector 114.

At 220, an estimated treatment delivery device output based on the measurement information and calibration information for scattered radiation detector 114 can be determined. The calibration information can be generated by known techniques, for example, using a calibrated detector and generating calibration factors, tables, etc., under a variety of operating conditions of the treatment delivery device 102. The calibration information can then be applied to the measurement information to transform the measurement information into an estimate of the treatment delivery device output.

At 230 collimator position information can be acquired. The collimator position information can include, for example, information on the leaf positions of a multi-leaf collimator, or any other configuration information appropriate for the type of collimator 108 being used. Collimator position information may be derived from treatment delivery device log files, detectors residing behind the patient, other imaging systems such as CT or MRI, and the like.

At 240 gantry angle position information can be acquired, for example, from treatment delivery device log files or other independent measurement devices.

At 250 patient imaging data can be acquired, for example, through CT or MRI systems utilized before, during or after patient treatment.

At 260, the dose received by the patient can be calculated by independent dose calculator 116 based on the estimated treatment delivery device output, acquired collimator position information, gantry angle position information, and patient imaging data. All of the above factors, transforms, calibrations, etc., can be utilized by computer software to make an independent calculation of the dose received by the patient. The calculations can be performed utilizing Monte Carlo, convolution/superposition or other methods, as noted above.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

Implementations of the current subject matter can include, but are not limited to, methods consistent with the descriptions provided herein as well as articles that comprise a tangibly embodied machine-readable medium operable to cause one or more machines (for example, computers, etc.) to result in operations implementing one or more of the described features. Similarly, computer systems may also be utilized that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (for example, the Internet, a wireless wide area network, a local area network, a wide area network, a wired network, or the like), via a direct connection between one or more of the multiple computing systems, etc.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. The present disclosure contemplates that the calculations disclosed in the embodiments herein may be performed in a number of ways, applying the same concepts taught herein, and that such calculations are equivalent to the embodiments disclosed. Furthermore, the above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A radiation therapy dose calculation system for use with a treatment delivery device for treating a patient, the radiation therapy dose calculation system comprising:

a scattered radiation detector comprising at least one programmable processor configured to determine measurement information during a patient treatment, the measurement information for use with an independent dose calculator when determining an estimate of an output of the treatment delivery device; and the independent dose calculator configured to:
acquire measurement information from the scattered radiation detector,
determine the estimate of the output of the treatment delivery device from the scattered radiation detector's determined measurement information,
acquire gantry angle and collimator position information utilized during the patient treatment,
receive patient imaging data, and
calculate a delivered dose to the patient from the gantry angle position information, collimator position information, patient imaging data and the estimate of the output of the treatment delivery device.

2. The system of claim 1 wherein the independent dose calculator is configured to acquire gantry angle and collimator position information from at least one log file associated with the treatment delivery device.

3. The system of claim 1 wherein the independent dose calculator is configured to acquire collimator position information from an electronic portal imaging device.

4. The system of claim 1 wherein the gantry angle information is acquired from an inclinometer.

5. The system of claim 1 wherein the scattered radiation detector comprises a radiation sensitive diode.

6. The system of claim 1 wherein the imaging data comprises CT data.

7. The system of claim 1 wherein the imaging data comprises MM data.

8. The system of claim 1 wherein the independent dose calculator is configured to calculate delivered dose to the patient utilizing Monte Carlo or convolution/superposition methods.

9. The system of claim 1 wherein the scattered radiation detector further comprises shielding to limit directions from which radiation is detected.

10. A computer program product comprising a non-transitory machine-readable medium storing instructions that, when executed by at least one programmable processor, cause the at least one programmable processor to perform operations comprising:
determining measurement information at a scattered radiation detector;
determining an estimate of an output of a treatment delivery device based on the measurement information and on calibration information for the scattered radiation detector;
acquiring collimator position information;
acquiring gantry angle position information;
acquiring patient imaging data; and
calculating a dose received by a patient based on the estimate of the output of the treatment delivery device, collimator position information, gantry angle position information, and patient imaging data.

11. The computer program product of claim 10 wherein the gantry angle and collimator position information are acquired from at least one log file associated with the treatment delivery device.

12. The computer program product of claim 10 wherein the collimator position information is acquired from an electronic portal imaging device.

13. The computer program product of claim 10 wherein the gantry angle information is acquired from an inclinometer.

14. The computer program product of claim 10 wherein the patient imaging data comprises CT data.

15. The computer program product of claim 10 wherein the patient imaging data comprises MM data.

16. The computer program product of claim 10 wherein calculating the dose received by the patient is performed utilizing Monte Carlo or convolution/superposition methods.

17. A radiation therapy dose calculation system for use with a treatment delivery device for treating a patient, the radiation therapy dose calculation system comprising:
a scattered radiation detector configured to acquire measurement information during a patient treatment, the scattered radiation detector comprising at least one programmable processor configured to perform operations comprising determining an output based on the measurement information, and
an independent dose calculator configured to:
acquire the measurement information from the scattered radiation detector,
determine an estimate of an output of the treatment delivery device from the scattered radiation detector's acquired measurement information,
acquire gantry angle and collimator position information utilized during the patient treatment,
receive patient imaging data, and
calculate a delivered dose to the patient from the gantry angle position information, collimator position information, patient imaging data and the estimate of the output of the treatment delivery device.

18. The system of claim 17 wherein the independent dose calculator is configured to acquire collimator position information from an electronic portal imaging device.

19. The system of claim 17 wherein the scattered radiation detector comprises a radiation sensitive diode.

20. The system of claim 17 wherein the scattered radiation detector further comprises shielding to limit directions from which radiation is detected.

* * * * *

UNITED STATES PATENT AND TRADEMARK OFFICE
CERTIFICATE OF CORRECTION

PATENT NO. : 10,099,067 B2  
APPLICATION NO. : 14/973570  
DATED : October 16, 2018  
INVENTOR(S) : Jeffrey M. Kapatoes, Thomas Allen Simon and William E. Simon Page 1 of 1

It is certified that error appears in the above-identified patent and that said Letters Patent is hereby corrected as shown below:

In the Claims

In Claim 7  
Column 7, Line 34:  
Replace "comprises MM data."  
With --comprises MRI data.--

In Claim 15  
Column 8, Line 19:  
Replace "comprises MM data."  
With --comprises MRI data.--

Signed and Sealed this  
Second Day of April, 2019

Andrei Iancu  
*Director of the United States Patent and Trademark Office*